United States Patent [19]

Brummet et al.

[11] Patent Number: 5,719,056
[45] Date of Patent: Feb. 17, 1998

[54] PROTEINS FROM *PYROCOCCUS FURIOSUS*

[75] Inventors: Shauna R. Brummet, Wadsworth, Ohio; Frank T. Robb, Silver Spring, Md.; Kimberly M. Borges, Coventry, Conn.; Kristine M. Hujer, Cleveland; Sally T. Domke, Parma, both of Ohio

[73] Assignee: Amersham Life Science, Inc., Cleveland, Ohio

[21] Appl. No.: 636,928

[22] Filed: Apr. 24, 1996

[51] Int. Cl.[6] .................... C12N 15/63; C12N 15/11; C12N 15/55; C12N 9/16

[52] U.S. Cl. ............... 435/320.1; 435/69.1; 435/172.3; 435/191; 435/196; 435/212; 435/252.3; 536/23.1; 536/23.2; 536/23.7

[58] Field of Search ................... 536/23.1, 23.2; 435/212, 320.1, 69.1, 172.3, 196, 252.3

[56] References Cited

PUBLICATIONS

Altschul et al., "Basic Local Alignment Search Tool," *J. Mol. Biol.* 215:403–419 (1990).

Gish and States, "Identification of protein coding regions by database similarity search," *nature genetics* 3:266–272 (1993).

*Primary Examiner*—Robert A. Wax
*Assistant Examiner*—Elizabeth Slobodyansky
*Attorney, Agent, or Firm*—Lyon & Lyon LLP

[57] ABSTRACT

Purified nucleic acid comprising a nucleotide base sequence selected from sequence ID NOS.: 1–9.

2 Claims, No Drawings

PROTEINS FROM *PYROCOCCUS FURIOSUS*

The work described in this application was to some extent supported by the U.S. government, specifically NSF Grant BCS9011583 and ONR Grant N00014-90-J-1823. The U.S. government may have rights in the invention.

BACKGROUND OF THE INVENTION

This invention relates to the cloning of nucleic acid from thermophilic organisms.

SUMMARY OF THE INVENTION

This invention features the cloning and sequencing of nucleic acid from *Pyrococcus furiosus*. Specifically, nucleic acid related to enzymes which have utility in several standard procedures: cloning, DNA fingerprinting, DNA/protein interaction studies, DNA repair functions, protein degradation, deamination of amino acids, preparation of deoxynucleotide, preparation of novel amino acids, and preparation of novel aldehydes.

In a first aspect, the invention features purified nucleic acid including a nucleotide base sequence selected from those shown as sequence ID NOS. 1–9. Preferably, such nucleic acid encodes an active enzyme, and is cloned by standard techniques as described herein.

By "purified" is meant that the nucleic acid is isolated from the environment in which it naturally occurs, that is, from a *Pyrococcus furiosis* cell, and is preferably provided within a vector such as a plasmid, cosmid or lambda vector, in which it can be expressed in other cells, e.g., *E. coli*. Such expression will allow production of large amounts of purified proteins which can be used in the standard methods noted above.

Other features and advantages of the invention will be apparent from the following description of the preferred embodiments thereof, and from the claims.

DESCRIPTION OF THE PREFERRED EMBODIMENTS

Over the last few years, several genera of bacteria have been discovered that grow near or above 100° C. All of these organisms are Archaea that have been isolated mainly from sulfurous geothermal marine environments. The group as a whole has many unique features such as ether-linked lipid membranes, introns and a transcriptional system more related to lower Eukaryotes (Eukarya) than to Prokaryotes. The DNA replication systems in the hyperthermophiles have not been characterized, and they are very likely to be extraordinary in comparison with other bacteria in terms of thermostability and error correction.

The hyperthermophilic microorganism, *Pyrococcus furiosus*, has the ability to survive and grow optimally at 100° C. (212° F.). Previous gene cloning and sequencing exercises demonstrated that genes could be identified by homology search with existing databases. The current invention is an example of gene discovery through sequence determination of random DNA clones leading to the simultaneous identification and cloning of genes.

The sequences of these genes, which are homologous to subtilisin (a serine protease), carboxypeptidase (a metal containing or serine protease), Dde I methylase (a nucleic acid modifying protein), RAD-2 (a DNA excision-repair enzyme), glycine dehydrogenase (a decarboxylating enzyme), ribonucleotide reductase (a nucleic acid modifying protein), L-asparaginase (an amido hydrolase), and alcohol dehydrogenase, may be used in expression of these enzymes in *Escherichia coli* or other systems. This may lead to an enhanced capacity to exploit the protein degradation and other protein-protein interaction capabilities of thermophilic organisms as well as their, potentially different, DNA repair mechanisms. The preparation of novel deoxy-nucleotides might be made possible from the ribonucleotide reductase protein, novel amino acids using the L-asparaginase homolog, and novel aldehydes utilizing the alcohol dehydrogenase homolog.

The following Example is provided for further illustrating various aspects and embodiments of the present invention and is in no way intended to be limiting of the scope.

EXAMPLE

Sequences of Random DNA Clones

The library contained insert DNA consisting of a mixture of partial restriction endonuclease digestions of DNA. Freshly isolated *Pyrococcus furiosis* genomic DNA (4 ug) was partially digested with each of the four enzymes Dra I, EcoR V, Hinc II, and Pvu II, to yield the majority of fragments in the 6–8 kbp size range, and the digestion reactions were pooled. The pooled DNA was methylated at EcoR I sites by incubation at 37° C. for 2 hr with 600 U EcoR I methylase (New England Biolabs, Beverly, Mass.) in 1× methylase buffer (supplied with enzyme), containing 100 ug/ml BSA and 80 uM S-adenosylmethionine in a 230 ul reaction volume. The reaction was stopped by incubation at 65° C. for 20 min. Phosphorylated 8-mer EcoR I linkers (15 ug) (Amersham Life Science, Inc., Cleveland, Ohio) were ligated to the pooled digested DNA (16 ug) by pre-incubation at 37° C. for 10 min in 1× ligase buffer, followed by addition of 180 Weiss units of T4 DNA ligase (Amersham Life Science, Inc.) and incubation at 16° C. for 18 hr. The ligated genomic DNA-linker mixture was digested with EcoR I (900 U) at 37° C. for 2 hr to create EcoR I ends on the insert DNA. Excess linkers were removed by filtration through Centricon 100 spin columns (Amicon, Beverly, Mass.). Insert DNA was ligated with Lambda Zap II EcoR I-digested vector. The library was packaged using Gigapack II packaging extracts (Stratagene, La Jolla, Calif.). The amplified genomic library was converted to pBluescript II plasmids following manufacturers instructions (Stratagene).

DNA was prepared on a VISTRA Labstation 625 (Molecular Dynamics/Amersham Life Science). Cultures (3 ml) grown in 2× YT broth were loaded directly into vials on the magnetic platform side of the Labstation for plasmid purification using the FMP DNA isolation method and the Automated Plasmid Template Preparation kit (Amersham Life Science).

Fluorescent sequencing reactions were performed on a VISTRA Labstation 625 using the PRISM Ready Reaction Dye Primer Cycle Sequencing kit with either M13 (−21) or M13 Reverse primers (Applied Biosystems, Foster City, Calif.). Reactions were run on an ABI 373A sequencing instrument and sequencing data were transferred to DNASIS software (Hitachi) for analysis. Sequencing data, BLAST outputs and annotation were compiled in a relational database (FileMaker Pro, Claris, Santa Clara, Calif.).

To identify the randomly sequenced DNA sequences, homology searches were performed with the BLAST algorithm (Altschul et al., (1990), J. Mol. Biol. 215: 403–410; Gish et al., (1993) Nature Genetics 3: 266–272), using the BLAST network service of the National Center for Biotechnology Information (NCBI). Briefly, sequences were first submitted to a search by BLASTX which translates the sequence of interest into the six possible reading frames and compares these sequences with a peptide sequence database. Homologies are considered to be significant if P(N) is less than 0.05—i.e., less than 5% probability of similarity occurring by random chance. For protein homologies, the codon bias of *Pyrococcus furiosus* was also taken into consideration. If a translated sequence contained multiple codons which are rare in *Pyrococcus furiosus* coding sequences, the homology was considered spurious.

Sequences identified as coding for proteins (enzymes) were the following:

SEQ ID NO: 1 Subtilisin
SEQ ID NO: 2 Carboxypeptidase
SEQ ID NO: 3 Dde I methylase
SEQ ID NO: 4 RAD-2 (FLAP endonuclease)
SEQ ID NO: 5 Glycine Dehydrogrenase
SEQ ID NO: 6 Ribonucleotide reductase
SEQ ID NO: 7 Ribonucleotide reductase
SEQ ID NO: 8 Alcohol Dehydrogenase
SEQ ID NO: 9 L-asparginase These partial DNA sequences can be used as probes for isolating the complete gene sequences from a library of *Pyrococcus furiosus* genomic DNA or cDNA. The presence of a low level of sequencing errors (if any) in any of SEQ ID NOS: 1-9 creates no difficulties in those procedures, since a probe based on one of the sequences of SEQ ID NOS: 1-9 will still specifically hybridize with the corresponding genomic DNA or cDNA under stringent conditions, and can be used to help resequence the DNA to confirm the probe sequence or discover any errors in the sequence. Such specific hybridization is the only required element in obtaining the genomic DNA or cDNA of interest. It is then possible to isolate the native proteins, or cloned or recombinant proteins.

Dde I methylase—this sequence encodes a DNA modification methylase with multiple matches to a specific restriction/modification system, Dde I, in bacteria. A thermostable methylase can be useful in cloning, DNA fingerprinting and DNA/protein interaction studies.

RAD-2 (FLAP endonuclease)—this sequence encodes a protein with significant homology to a DNA excision-repair endonuclease which can be used in studying DNA repair functions in thermophiles which may be different from that found in mesophiles.

Subtilisin and carboxypeptidase—each of these sequences encodes a protein which shows significant homology to protein degrading enzymes from bacteria and eukaryotes. Each can find use in high temperature studies of degradation of proteins. Carboxypeptidase is known to be a Zn containing enzyme in many organisms but in yeast it is known to not require a metal in its active site, but instead function more similarly to serine proteases. This enzyme could be important in the study and use of the Zn- or serine-proteases. Potential industrial scale use could be made of these thermostable degradative enzymes.

Glycine dehydrogenase—this clone encodes a sequence with strong homology to known eukaryotic dehydrogenases. The clone can be used to isolate the full length nucleotide sequence which might be useful for computer-aided design of novel deaminating amino acid dehydrogenases.

Ribonucleotide reductase—a full length sequence can be obtained from the library using SEQ ID NO. 7 or SEQ ID NO. 8 as a probe. The enzyme can be used for the preparation of deoxy nucleotides.

L-asparaginase—a full length clone can be obtained from the library using this sequence as a probe. The enzyme can be used for the preparation of novel amino acids.

Alcohol dehydrogenase—a full length clone can be obtained from the library using this sequence as a probe. The enzyme can be used for the preparation of novel aldehydes.

The DNA sequences can also be used to isolate homologous sequences from a wide variety of organisms. Although only a few such homologies at the DNA level were found in our searches, this may be due to a lack of similar sequences in the database, rather than a lack of similarity between organisms at the nucleotide level. Translation of the sequences can be used to design peptides for antibody production, or to design nucleotide probes with a codon bias similar to the organism in which the desired search is to be made.

Other embodiments are within the following claims. Thus, while several embodiments have been shown and described, various modifications may be made without departing from the spirit and scope of the present invention.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 395 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
        base.

( x i ) SEQUENCE DESCRIPTION: SEQ ID NO:1:

```
GAATTCCTCT AACTGTATTG GTACTCATAT CGTCAAATGT TCCAACTGGA AGTACTTTNC         60
```

```
CGTACTTGAG ATAGTATGCA GCTTGAATTA GCGCAACAAC ACCACTTACG TGAGGNGTTG      120

CCATACTTGT ACCTGAAAGA GTTTCATAAG TNTCGTCTGG ATAAGTGCTA AGTATATCAA      180

CACCTGGNGC GCTAACTTCT GGCTGACGAT TGCTCCAGTA CGGGACTTGG TCATTTATAT      240

CAGTAGCCCC TACTGCAATT ACTTCAGGAT AGGCTGCTGG ATAACTGGG  CTAGAGGCTC      300

CTTCATTGCC AGCCGCTGCA ACTATAACTA TTCCCGCTTC GTAGGGCCTT CTTAATGATC      360

TCGTGAAGGT AAGTATCATC TGCAGATNCC TCCTA                                 395
```

(2) INFORMATION FOR SEQ ID NO:2:

(i) SEQUENCE CHARACTERISTICS:
        (A) LENGTH: 344 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:2:

```
GAATTCCTTG AGCTCATATA CCCAGTTTTA AAAGAGAACT TACCCTTCAT GTCGAACTAC      60

ACACCTGAAG ATGTCTACCT ATACTTCAAC ATAGTCAGGC CCGATTTCAT AAGAACTGAG      120

GCCGACGTAG TGACATACAA CTTCCACATA TTGCTCCGCT TTAAGCTAGA GAGACTAATG      180

GTGAGTGANG AGATAAAGGC AAAGGATCTT CCAGAGATGT GGAATNATGA AATGGAGAGA      240

CTTCTTGGGA TAAGNCCCAG GAAGTACTCA GAAGGTATCT TACAAGACAT TCACTGGGCA      300

CATGGAAGCA TAGGATACTT CCCCACGTAC ACGATAGGGA CACT                       344
```

(2) INFORMATION FOR SEQ ID NO:3:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:3:

```
GAATTCTAAA ACTAACCTGC CTATTGGNTC TCTGTACAGC CTATCCTTTG GATTCTCCAT      60

TCTTCTGGAA TTTATAGCTG TAAATGGCTC ACANGGGGC  CCTCCAATTA TAACATCAGC      120

TTTTGGAAAA TCTTTGGGGT TTAGAGCCTT TATATCGGAA ACGTACACTT TAACCTCGGG      180

AAAATTAAAG GAGTAAGTCT TGGCTTTTGG CTTAAAATTT TCAACTGCAG AGATAATTTT      240

GANTCCAGCA AGTTTAAATC CAAGAGAAAA GCCTCCAGCT CCAGCAAAAA GANTCANTAA      300

NCAGANGGNA TTCCAGCTCT TTCAACCGNN TTTNTTCCCA TGGCCTTTAA AAACTTCCTT      360
```

(2) INFORMATION FOR SEQ ID NO:4:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (ix) FEATURE:
        (D) OTHER INFORMATION: The letter "N" stands for any base.

(xi) SEQUENCE DESCRIPTION: SEQ ID NO:4:

```
GAATTCCTAT AGTTCAAGCA CCTAGNGNNG GAGAGGCCCA AGCTGCATAT ATGGCCGCAN    60

NGGGGAGCGT GTATGCATCG GCTAGTCAAG ATTACGATTC CCTACTTTTT GGAGCTCCAA   120

GACTTGTTAG AAACTTAACA ATAACAGGAA AAAGAAAGTT GCCTGGGAAA AATGTCTACG   180

TCGAGATAAA GCCCGAGTTG ATAATTTNGG AGGAAGTACT CAAGGAATTA AAGCTAACAA   240

GAGAAAAGCT CATTGAACTA GCAATCCTCG TTGGGAACAG ACTACAACCC ANGGAGGAAT   300

AAAGGGCATA GGCCTTAAAA AAGCTTTAGA GATTGTTAGA CACTCAAAAG ATCCGCTAGC   360

AAAGTTCCAA AAGCAAAGCG GTGTTGGNTT TATATGCAAA TAAAAGGGTT TCTTTCCTAA   420

ACCNCACCAG GTCACAGNTN ACTACAATTT AGGTG                              455
```

( 2 ) INFORMATION FOR SEQ ID NO:5:

( i ) SEQUENCE CHARACTERISTICS:
        ( A ) LENGTH: 442 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any
        base.

( x i ) SEQUENCE DESCRIPTION: SEQ ID NO:5:

```
GAATTCTTGG AAAGATAAGG CCTGGAGACA TGGGATTTNA CATTGTGCAC CTCAACCTCC    60

ACAAGACGTT TTCAACTCCT CACGGTGGAG GAGGTCCAGG GGCTGGGCCC GTAGNAGTTA   120

AAGAGTTTCT GAAAGATTAT CTACCAGTGC CACTGGTGAG TTATGACGAG AAAAGCGGTA   180

GGTATTACCT TGACTACAAC GTGCCAAAGA GCATTGGAAA GGTGAAGGAG CTTTATGGAA   240

ACTTTGCAGT TCTTGTGAGG GCATTAACTT ACCTTAAGAT AATGGGAAGA GATGGCCTGA   300

GAGAAGTGAG TGAGATAGCA GTTTTAACCG CAAACTATCT AACCCAAAGC TCAAGGGGNC   360

AAGGGGTATC TCTCCNGGGA AAGGCTCAGG AAGCNCGAGT TGTATTCTCA GCAGACCCNT   420

GAGGAAGGGC CTGGGTTAAA CC                                            442
```

( 2 ) INFORMATION FOR SEQ ID NO:6:

( i ) SEQUENCE CHARACTERISTICS:
        ( A ) LENGTH: 391 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for any
        base.

( x i ) SEQUENCE DESCRIPTION: SEQ ID NO:6:

```
GAATTCCATA CAACAGCNAA GAAGGCTTCA AGTTCATGAG GAAAGTCACC GAATACCTAA    60

CCTTCTACGC CTACAAGTAC AGCGTCGAAG CTGCCANGNN GAGGGAACC TTCCCACTCT    120

ACGACAAGAC CGAATATCCA GAGGGTAAGC TACCCGTGGA GGGCTTCTAC CACCCAGAGA   180

TATGGAACCT TCCATGGGAT AAGCTCGTCG AGGAGATAAA GAAGTATGGG CTCAGGAATG   240

CAATGGTTCA CGACGTGCCC ACCGACCGGT AGCGTTTCGA TGATAGCCGA CACCTCAAGC   300

GGAATTGAAC CGGTCTATGC ACTCGTCTAC AAGAAGAGTG TTACCGTTGG TGAATTCCTG   360

CAGCCCGGGG GATCCACTAG TTTCTAGAGC G                                  391
```

( 2 ) INFORMATION FOR SEQ ID NO:7:

( i ) SEQUENCE CHARACTERISTICS:
    ( A ) LENGTH: 412 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

( x i ) SEQUENCE DESCRIPTION: SEQ ID NO:7:

| | | | | | | |
|---|---|---|---|---|---|---|
| GAATTCCCAG | CTTGAAGAGC | GCATCGGCAA | GTCCATCAT | TCCAACTCCG | ATCCTCCTCG | 60 |
| TCAGCTTCGT | GTTGTAATCT | ATCTCTGGCA | ACGGAACTT | GTTGACGTCT | ATGGAGTTGT | 120 |
| CAAGGTACTT | AGCAACCTTT | TGAATCACGT | ATGCATATTC | ATCCCAATCG | AAGTACGGCT | 180 |
| TTCCGTTCTC | GTCGTACTTG | ACGAACTTGG | CCAAATTGAT | CGATGCGAGG | TTACAGGATT | 240 |
| CGTATTCGTA | TAGAGGCTCT | TCTCCACAGT | TGTGGCTCAT | GAAGCCGTTG | CTTATGTACA | 300 |
| TGTGATAATT | GGGAACCGTG | AAGTCATAGA | CTATTTNCCT | TTCCAAGCAA | CTCAACGGTT | 360 |
| CTCAACCGTG | ACAATTGGGT | GGTCAACCTT | GGTCTTCTTN | AGGGTTGAGG | TT | 412 |

( 2 ) INFORMATION FOR SEQ ID NO:8:

( i ) SEQUENCE CHARACTERISTICS:
    ( A ) LENGTH: 341 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

| | | | | | | |
|---|---|---|---|---|---|---|
| GAATTCTTTC | TCCGTTCGGA | AAGGCTCTAA | CTATGACGAA | CTGTCCTGGC | TGAACTTTTT | 60 |
| TAGCTACGTG | AGGTGCGTAA | ACTTTATACC | AGGTATTTCT | CATTGCGATT | TCCTTTTTCT | 120 |
| CGAGGATTTT | ATACATGATG | AACACCTCCG | ATCACGTGAA | CATTTTGAA | CATACTCAAA | 180 |
| TGTTGTGAAC | ATTGAGTGTT | TATAAAGATA | TTGTAAACCA | AAGGTTATAG | AGCATAAGAG | 240 |
| AAAATTACTT | AAATCCCTTG | AATATGAAGG | TGCGATGACA | AAAGTATACA | TTGAGAACTA | 300 |
| TGGATGTGCG | AGAAATAGAG | CAGATGGAGA | GATTATGGCA | G | | 341 |

( 2 ) INFORMATION FOR SEQ ID NO:9:

( i ) SEQUENCE CHARACTERISTICS:
    ( A ) LENGTH: 364 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

( x i ) SEQUENCE DESCRIPTION: SEQ ID NO:9:

| | | | | | | |
|---|---|---|---|---|---|---|
| GAATTCCTCC | ANNTCCATAA | CCTNCTATGN | CAATTCCTCT | ATANNCCAGC | TCTACAGCTG | 60 |
| CCCTAAATAT | GTCCCCCGAA | AGTCCTGGGA | TTAGCTTTAT | AACTAGAACT | TTTGGATCGT | 120 |
| GCCTAGGCCT | AATGTGACTT | CTCCATTGTN | AAACTTNGGA | ATAAAGTTAA | CCACGAGATC | 180 |
| TTCTCCTCTT | AATTCTGCAG | TTATAGGGTA | GTTAATGCTT | TCGAATGCAT | NTCTGCTCAT | 240 |
| TGTCCTAACC | TTAGATGTTC | TAACTCCAAG | CATAACTTTT | CCATTGANGG | CCACGTAAAC | 300 |
| TTCCCTAANT | CCAGAAGTTG | CAAACTTTAT | TGCTGTTTGC | AAGTTTAGGG | GGGCATCACT | 360 |
| ATTT | | | | | | 364 |

We claim:

1. Purified nucleic acid comprising a nucleotide base sequence selected from sequence ID NOS.: 1–9 in a vector.

2. The purified nucleic acid of claim 1 encoding an enzyme from *Pyrococcus furiosus*.

* * * * *